US005674238A

United States Patent [19]
Sample et al.

[11] Patent Number: 5,674,238
[45] Date of Patent: Oct. 7, 1997

[54] PERINEOMETER

[75] Inventors: Steven B. Sample, San Marino; Bonnie Bullough, Northridge, both of Calif.; Patricia A. Burns, Clarence, N.Y.

[73] Assignee: Research Foundation of the State Univ. of N.Y., Amherst, N.Y.

[21] Appl. No.: 668,800

[22] Filed: Jun. 24, 1996

Related U.S. Application Data

[63] Continuation of Ser. No. 243,035, May 16, 1994, abandoned.

[51] Int. Cl.$^6$ .................................................. A61M 25/00
[52] U.S. Cl. ........................... 606/192; 604/96; 128/778
[58] Field of Search .............................. 606/191, 192, 606/193, 194; 128/778; 604/96, 104

[56] References Cited

U.S. PATENT DOCUMENTS

| | | | |
|---|---|---|---|
| 1,826,284 | 10/1931 | Newton | 606/192 |
| 2,168,427 | 8/1939 | McConkey | 606/192 |
| 2,507,858 | 5/1950 | Kegel | 606/192 X |
| 2,541,520 | 2/1951 | Kegel | 606/192 X |
| 2,687,719 | 8/1954 | Hoyt | 606/192 X |
| 2,839,050 | 6/1958 | Sokol . | |
| 3,598,106 | 8/1971 | Buning . | |
| 3,640,284 | 2/1972 | DeLangis . | |
| 3,726,273 | 4/1973 | Cole . | |
| 3,752,150 | 8/1973 | Harris . | |
| 3,916,906 | 11/1975 | Gerry | 606/192 |
| 3,926,178 | 12/1975 | Feldzamen . | |
| 4,048,985 | 9/1977 | Sasse . | |
| 4,050,449 | 9/1977 | Castellana et al. . | |
| 4,141,364 | 2/1979 | Schultze | 606/192 X |
| 4,167,938 | 9/1979 | Remih . | |
| 4,216,783 | 8/1980 | Kaiser et al. . | |
| 4,476,880 | 10/1984 | Giem et al. . | |
| 4,653,514 | 3/1987 | Shapiro . | |
| 4,694,827 | 9/1987 | Weiner et al. | 606/192 |
| 4,768,522 | 9/1988 | Shapiro . | |
| 5,021,046 | 6/1991 | Wallace | 606/192 X |
| 5,201,753 | 4/1993 | Lampropoulos et al. | 606/191 X |
| 5,433,216 | 7/1995 | Sugrue et al. | 128/778 |

OTHER PUBLICATIONS

D. Mandelstam, Incontinence and its Management, (2nd ed. 1986), pp. 184–194 (authored by A. Shephard).

Dougherty et al., "An Instrument to Assess the Dynamic Characteristics of the Circumvaginal Musculature" Nursing Research vol. 35, No. 4, 202–206.

InCare Medical Products advertising brochure entitled "Introducing the PRS8900 System".

Swan Attika (Pty) Ltd advertising brochure for the CC–2BF system.

*Primary Examiner*—Sam Rimell
*Attorney, Agent, or Firm*—Seed and Berry LLP

[57] ABSTRACT

A perineometer which indicates the pressure created by vaginal contractions. A probe with a bulbous end is inflated inside the vagina, and a pressure transducer in fluid communication with the probe indicates the pressure of vaginal contractions to a display. The probe may be constructed with bellows. The probe may also be constructed of an elastic material having two different expansion rates.

46 Claims, 5 Drawing Sheets

PERINEOMETER

This application is a continuation of application Ser. No. 08/243,035, filed May 16, 1994, now abandoned.

TECHNICAL FIELD

The present invention relates generally to perineometers, and in particular to an improved perineometer having a pneumatic probe which can be inserted in a patient's vagina and thereafter inflated to an expanded configuration which will maintain it in position, and a control module which displays indicia related to the degree of contraction of the patient's vaginal musculature so as to enable her to obtain immediate and comprehensive feedback and guidance with respect to her vaginal muscular contractions, thereby enabling her to optimize the strengthening of her vaginal musculature through exercise.

BACKGROUND OF THE INVENTION

Urinary stress incontinence is an involuntary loss of urine caused by relaxation of the pelvic musculature. The incontinence occurs during episodes of increased intra-abdominal pressure such as coughing, sneezing, laughing, or lifting. Urinary stress incontinence is the most common urological problem in women over 50. Two major treatment modalities are currently used to treat the condition: surgical repair, and exercises of the pubococcygeal muscle. The exercise modality was developed and popularized in the late 1940s by a California obstetrician/gynecologist, Arnold Kegel, who traced the idea back to exercises taught by midwives and early obstetricians.

Traditionally the contractile strength of the vaginal musculature was assessed by physicians as a part of the routine gynecological examination. The anterior portion of the pubococcygeal muscle was located with the tip of the index finger behind the pubic os. The posterior portion of the pubococcygeal muscle was felt in the vaginal midline anterior to the coccyx. Strength was assessed by asking the patient to contract the vaginal musculature as though she were stopping the flow of urine. Strength was evaluated in relation to norms developed through clinical practice. Relaxation of the vaginal musculature was further assessed by noting the position of the uterus, prolapsed or not, and the presence or absence of a cystocele or a rectocele.

The exercises developed by Kegel were aimed at strengthening the vaginal musculature, including most particularly the pubococcygeal muscle. As an aid to his teaching program, he developed an instrument which he called a perineometer. Its purpose was to measure the strength of the pubococcygeal muscle and to serve as a resistant force against which the muscle could be contracted.

The Kegel perineometer included a pneumatic vaginal probe and an attached mechanical manometer calibrated from 0 to 100 mm of mercury. The vaginal probe was constructed using a hollow steel tube having flanges on each end as the central core. An anode-processed rubber cot or sheath was fitted loosely over this tube, thereby creating a compressible rubber air chamber that measured approximately 2 cm in diameter and 8 cm in length. The base of the probe was fitted with a rounded semi-rigid shield, 8 cm in diameter, which rested against the perineum when the probe was inserted in the vagina. The probe was connected to the manometer with rubber tubing. Measurement of the contractile strength of the vaginal musculature was accomplished by inserting the probe into the vagina, asking the patient to contract voluntarily the muscles of her vagina around the probe, and reading the resultant change in pressure on the manometer.

Kegel found that practically all women who exhibit urinary stress incontinence also exhibit flaccidity and/or atrophy of the vaginal musculature. His research showed that an appropriate exercise regimen carried out in conjunction with the Kegel perineometer would sufficiently strengthen the vaginal musculature so as to effectively eliminate urinary stress incontinence in most patients. Subsequent studies confirmed this relationship. Eventually these exercise regimens came to be called Kegel exercises, whether or not they were carried out in conjunction with the Kegel perineometer.

The Kegel perineometer suffered from several drawbacks. First, Kegel's vaginal probe was of a single fixed size, and was relatively large. Many women, and most especially older women, were reluctant to self-insert such a large device into their vaginas. Moreover, some women experienced discomfort or even pain during the process of insertion.

Because of the tapered shape of Kegel's vaginal probe, there was a tendency for the probe to be expelled during vaginal contractions. This tendency made it necessary for the patient to keep her hands continuously on the base of the probe while performing her Kegel exercises, and thus in continuous contact with her own vulva, a practice which many patients found to be distasteful.

There was no provision with the Kegel perineometer for establishing a predetermined base-line pressure in the vaginal probe when the patient's vaginal muscles were relaxed. Then too, the mechanical manometer in the Kegel perineometer was somewhat difficult for the patient to read, both because the numbers and graduations were necessarily small to accommodate the full range of possible pressures on the dial face, and because short-term fluctuations in the strength of the patient's vaginal contractions could give rise to rapid and erratic movements of the manometer's indicating needle. And finally, the Kegel perineometer had no provisions for assisting the patient in timing or regulating the duration of her vaginal contractions, or for calculating the average strength thereof.

A variant of Kegel's device is described in U.S. Pat. No. 2,507,858 issued May 16, 1950, which discloses an uninflated insertable member which is used to indicate pneumatically the change in pressure on an associated dial gage. U.S. Pat. No. 2,541,520, issued Feb. 13, 1951 to A. H. Kegel illustrates a similar type of apparatus except that the applicator is inflatable via a pneumatic bulb.

A variant of Kegel's perineometer was developed by Wilfred Lynch Associates of Racine, Wis. This device, called a pelvic floor exerciser, included a vaginal probe consisting of a sponge covered by a balloon. The probe is contracted prior to insertion by evacuating most of the air out of the probe by means of a hand-operated syringe. The patient then removes the syringe, caps off the opening to the probe, inserts the probe in her vagina, allowing the probe to expand by uncapping the opening to the probe, and connects the opening in the probe to a flexible tube, which in turn is connected to a ball-in-tube meter that apparently measures the rate of change of pressure in the probe.

When the pelvic floor exerciser is in use, the patient must keep one hand on the probe to retain it in her vagina, and must with her other hand hold the meter so that the ball-in-tube portion is perpendicular to the ground. She then contracts her vaginal muscles and watches the ball as it rises and instantaneously falls again in response to the initial rate of change of her vaginal contraction. During the exercise the patient must perceive and record the maximum height reached by the ball in the tube. When her exercise session is completed, the patient goes through the uncorking and deflating process in reverse, in order to safely remove the probe from her vagina.

The difficulties inherent with the Lynch exerciser are numerous and obvious. It is not an improvement over the Kegel perineometer at all, except for the fact that the vaginal probe is reduced in size prior to insertion.

Another device for measuring the tone of the muscular system of the floor of the vagina is described in U.S. Pat. No. 2,839,050 issued Jun. 17, 1958 to K. Sokol. In this device, an inflatable rubber or plastic vaginal probe is used to detect muscular pressure which is measured pneumatically by a dial gage.

Another variant of Kegel's perineometer has been described by A. Shephard in her chapter entitled "Re-education of the Muscles of the Pelvic Floor" that appears in the book entitled *Incontinence and Its Management*. Very little information concerning this device is given in the book. Developed by Craig Medical, the device appears to have a cylindrical probe with a balloon at the end; the probe is connected to some sort of pressure-measuring gauge, which presumably is read by an attendant. The Craig device has no apparent advantages over Kegel's original perineometer.

Yet another variant of Kegel's perineometer has been developed recently by M. Dougherty at the College of Nursing of the University of Florida at Gainesville. The Dougherty device involves an elaborate and expensive compressible intravaginal balloon device (IVBD) that is custom made to fit the interior of a particular patient's vagina. The IVBD is pneumatically connected to a pressure-measuring device, the output of which is recorded on a strip chart.

The Dougherty device has no apparent advantages over the original Kegel perineometer, except for the developer's contention that her IVBD will not inadvertently slip out of the patient's vagina. However, the Dougherty device has many disadvantages, including that it is extremely expensive, requires a separate custom-fitted appliance for each patient, utilizes complex scientific instrumentation, and can only be used under the supervision of a skilled attendant.

Numerous types of perineometer-like devices are also described in the patent literature. For example, U.S. Pat. No. 3,598,106 issued Aug. 10, 1971 to E. Buning describes a noninflatable liquid-filled pressure indicating vaginal exerciser utilizing a conventional fluid pressure measuring device. U.S. Pat. No. 3,640,284 issued Feb. 8, 1972 to P. A. DeLangis describes an apparatus which measures vaginal pressure by means of a cylindrical condom holder filled with water and a manometer. U.S. Pat. No. 3,726,273 issued Apr. 10, 1973 to N. S. Cole teaches a vaginal exercising device consisting of inflatable bulbs having only slight expansion capability. Vaginal pressure is indicated by conventional pneumatic pressure indicators. U.S. Pat. No. 3,752,150 issued Aug. 14, 1973 to J. P. Harris discloses a device for exercising vaginal muscles using a liquid-filled pressurized insert wherein the pressure caused by muscular contraction is indicated on a conventional liquid pressure measuring device. U.S. Pat. No. 3,926,178 issued Dec. 16, 1975 to A. N. Feldzamen involves a device for exercising sphincter muscles, including vaginal muscles utilizing a noninflatable insertable member having two helical tubes. Readout of the pressure sensed by the probe may be by means of a conventional Bourdon tube, a liquid level pressure sensor, tubes filled with colored liquid or a conventional pressure gage.

U.S. Pat. No. 4,050,449 issued Sept. 27, 1977 to F. S. Castellana, et al., describes an air inflatable balloon-like insertable member including a collar to hold the inflatable member in place. Pressure is measured by means of a conventional dial pressure gage. U.S. Pat. No. 4,048,985 issued Sep. 20, 1977 to H. A. Sasse describes an air or liquid filled elongated tube probe which is directly connected to a pressure indicating gage. U.S. Pat. No. 4,167,938 issued Sept. 18, 1979 to H. Remih discloses a circumferentially expandable insertable body and a conventional air actuated mechanical indicator. Alternatively, an electronic display for digitally providing a pressure indication may be utilized. U.S. Pat. No. 4,216,783 issued Aug. 12, 1980 to H. Kaiser, et al., shows an insertable probe whereby vaginal pressure may be measured by a conventional air pressure gage in connection with biofeedback to increase the degree and strength of control exercised over the vaginal muscles. U.S. Pat. No. 4,476,880 issued Oct. 16, 1984 to D. A. Giem, et al., discloses an air pressure operated tubular member wherein air pressure is converted to an electrical signal by means of a transducer. By specifically disclosed electronic circuitry, a visual display of the vaginal pressure may be obtained. U.S. Pat. Nos. 4,653,514 issued Mar. 31, 1987 and 4,768,522 issued Sep. 6, 1988 to S. W. Shapiro describe insertable members which are partially deflated by means of a vacuum before insertion into the vagina. With these devices, pressure is measured by a conventional air gage.

A very different approach to measuring the contractile strength of the vaginal musculature involves electromyography (EMG). In this approach a set of electrodes is placed in physical contact with the interior walls of the patient's vagina. The electric potential differences among the probes are then measured by an electrometer, and from these measurements the degree of vaginal muscle contraction is inferred. Devices utilizing this approach are sometimes called vaginal myographs.

Several vaginal myographs are marketed by Biotechnologies, Inc. of Strafford, Pa. All of Biotechnologies' vaginal myographs utilize a dumbbell-shaped solid vaginal probe which is made of hard dental acrylic, and which has three silver pads embedded around the constructed central portion of the probe. The probe is inserted in the patient's vagina, and is then connected by an electric cable to an assortment of amplifiers, integrators, computers, video displays, printers, recorders, telephone modems, quantized lighted bar displays, and other such complex and expensive monitoring devices.

The Biotechnologies' vaginal myographs suffer from a wide range of inherent problems. First, they are extremely expensive—the probes alone cost $250 each, a transportable "clinical perineometer costs $3,000, and a complete system with its attendant computer costs nearly $8,000. Most of these devices can be operated only by a skilled health professional after extensive specialized training.

Further, there is no guarantee that these vaginal myographs do in fact measure the strength of contraction by the vaginal musculature. The level of electrical activity measured by these devices is determined by several variables, including the number of muscular motor units firing, the rate of firing, the proximity of the motor units to the electrodes, and the electrical characteristics of the vaginal fluid that forms the interface between the electrodes and the vaginal walls. These variables can give rise to misleading variations in readings from one woman to the next. For example, women with cystoceles will often have high EMG readings in spite of poor vaginal musculature, due apparently to the closer fit of the vaginal mucosa to the probe. The response of a vaginal myograph can also be affected by the contraction of muscles proximate to, but distinct from those surrounding the vagina, such as the gluteus maximus. Then too, because the electrical signals picked up by the probe are at the microvolt level, vaginal myographs are extremely sensitive to electromagnetic interference.

Another example of what appears to be a vaginal myograph is described by A. Shephard in her work noted above. Once again, very little information concerning this device is given in the book. Developed as an experimental unit by T. Floyd at the Clinical Investigation Unit of Ham Green Hospital in Bristol, England, the device apparently comprises a hard cylindrical probe with electrodes attached thereto, which electrodes are connected to an electrometer that reads out the potential difference between the electrodes on a simple meter. In general, the Floyd device suffers from all of the disadvantages of the Biotechnologies devices.

The present invention is designed to overcome all of the drawbacks, disadvantages, and difficulties inherent in these prior art approaches.

For example, in contrast to vaginal myographs, the present invention measures vaginal muscle contractions directly by means of a pneumatic probe. In contrast to all prior art, the preformed inflated shape of the probe in the present invention resembles that of a small tampon. The patient herself can easily adjust the pressure in the probe, so that it fits comfortably in her particular vagina. Once inflated, the probe stays in place in the vagina without the patient or an attendant having to hold it in place by hand. Further, the present invention utilizes disposable vaginal probes, thereby obviating the inconvenience of cleaning the probe after each use while simultaneously eliminating the possibility of infecting the patient's vagina by way of the probe.

The present invention is also easily operable by patients of average intelligence, education, and skill. It is completely self-contained and completely portable, and comprises only two small physical parts interconnected by a thin flexible tube. Embodiments of the present invention described herein contain an integrated-circuit microprocessor which leads the patient through her exercise routine and which, in conjunction with a pressure transducer and electronic circuitry, automatically computes an average value of her vaginal contractions while simultaneously providing real-time biofeedback from her vaginal musculature to her conscious will.

Finally, and perhaps most importantly, various embodiments of this invention can be manufactured very inexpensively, and thus will be readily accessible to the great mass of women who would benefit from its use.

SUMMARY OF THE INVENTION

Embodiments of this invention are intended to measure the strength of the pubococcygeal portion of the levator ani muscle and to assist women in learning to exercise this muscle and related vaginal musculature. A secondary purpose of the invention is to teach women to exercise the vaginal musculature in order to improve sexual functioning, particularly among those women whose less-than-optimal functioning is caused by poor vaginal musculature.

An important feature of this invention is the fact that it senses vaginal muscle contractions by means of a pneumatic vaginal probe which can be easily inserted by the patient herself, and which can then be inflated by the patient so that the probe offers the appropriate resistance to her vaginal contractions. The probe is constructed so that, once inflated, it will stay in the patient's vagina without having to be continuously held in place by the patient herself.

A second important feature of this invention is that the strength of contraction of the patient's vaginal muscles relative to their quiescent state is automatically calculated and indicated by a small self-contained control module which the patient can hold in her hand while she is performing her Kegel exercises. The control module electronically smooths the instantaneous values of the patient's vaginal contractions so that the numbers indicated change sufficiently slowly to permit them to be easily perceived by the patient. Thus this invention provides real-time biofeedback from the patient's vaginal muscles to her conscious will through her senses of sight or hearing, thereby improving the efficacy of her exercise regimen. Moreover, the control module assists the patient in timing and regulating the duration of her vaginal contractions, and automatically computes the average strength of each contractile cycle.

Yet another feature of this invention is that it can be easily and safely operated by patients of average education and experience, in their own homes, without on-site supervision, and with only minimal training and occasional oversight by a health professional. In particular, the quiescent pressure in the pneumatic probe can be easily and conveniently set by the patient herself through a procedure that requires no technical knowledge or skill on her part.

A final important feature of this invention is that it is relatively uncomplicated and inexpensive to produce, and thus can be sold at a price that is within reach of the vast majority of those women for whom vaginal exercises are indicated.

To achieve the foregoing and other objects, and in accordance with the purposes of the present invention as described herein, an improved perineometer is provided for measuring the strength of vaginal muscle contractions which utilizes a vaginal probe whose interior pressure may be varied by such contractions. The perineometer includes a control module which indicates alternating periods of exercise and rest so that the patient may contract her muscles according to a predetermined length of time separated by periods of rest. The controller also includes a means for indicating the difference between the probe interior pressure and a predetermined pressure during the period of exercise, as well as means for indicating the difference between the average pressure of the probe interior during a preceding exercise period and a predetermined pressure during a period of rest.

In accordance to a further aspect of the invention, the controller indicates during the periods of exercise the difference between the probe pressure during the current exercise period and the average probe pressure during the preceding rest period.

In accordance to another aspect of the invention, the controller indicates during the periods of rest the difference between the average pressure within the probe during the preceding exercise period and the average pressure within the probe during the preceding rest period.

In a still further aspect of the invention, the control module is also selectively operational in an adjust mode and a run mode and includes means for indicating while in the adjust mode when the pressure within the probe is greater than a predetermined pressure.

In yet another aspect of the invention, the vaginal probe includes a frame and an inflatable balloon. The inflatable balloon has an interior and includes a first end which defines an opening to the interior and which is secured to the frame.

The balloon is inflatable from a preformed configuration to an unconstrained expanded configuration in which the second end of the balloon has an effective perimeter which is larger than the effective perimeter of the intermediate portion of the balloon disposed between the two ends.

In a still further aspect of the invention, the balloon includes at least one longitudinal bellow which is disposed radially.

In accordance to yet another aspect of the invention, while the balloon is in the preformed configuration, the intermediate portion and the second end have a substantially uniform outside diameter which is substantially constant along the intermediate portion and second end of the balloon.

According to a still further aspect of the present invention, the depth of the bellows disposed on the second end, is greater than the depth of the bellows disposed on the intermediate portion, thereby allowing the second end to have a greater effective perimeter in the expanded configuration than the effective perimeter of the intermediate portion.

In yet another aspect of the invention, the control module includes means for inflating the balloon which is in fluid communication with the interior of the balloon.

In a still further aspect of the invention, the frame of the vaginal probe includes a hollow tube which is disposed at least partially within the balloon, and has a flange disposed intermediate the two ends of the tube.

Still other objects of the present invention will become apparent to those skilled in this art from the following description wherein there is shown and described a preferred embodiment of this invention, simply by way of illustration, of one of the best modes contemplated for carrying out the invention. As will be realized, the invention is capable of other different embodiments, and its several details are capable of modification in various, obvious aspects, all without departing from the invention. Accordingly, the drawing and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 2b is a cross-sectional view of the vaginal probe of FIG. 2a, approximately to scale, taken along line a—a of FIG. 2a.

FIG. 3b is a cross-sectional view of the vaginal probe of FIG. 3a, approximately to scale, taken along line c—c of FIG. 3a.

FIG. 4a is an enlarged cross-sectional view (approximately 3× actual size) taken along line a—a of FIG. 2a.

FIG. 4b is an enlarged cross-sectional view (approximately 3× actual size) taken along line b—b of FIG. 2a.

Reference will now be made in detail to the present preferred embodiment of the invention, an example of which is illustrated in the accompanying drawings.

DETAILED DESCRIPTION OF THE PREFERRED EMBODIMENT

Figure 1:
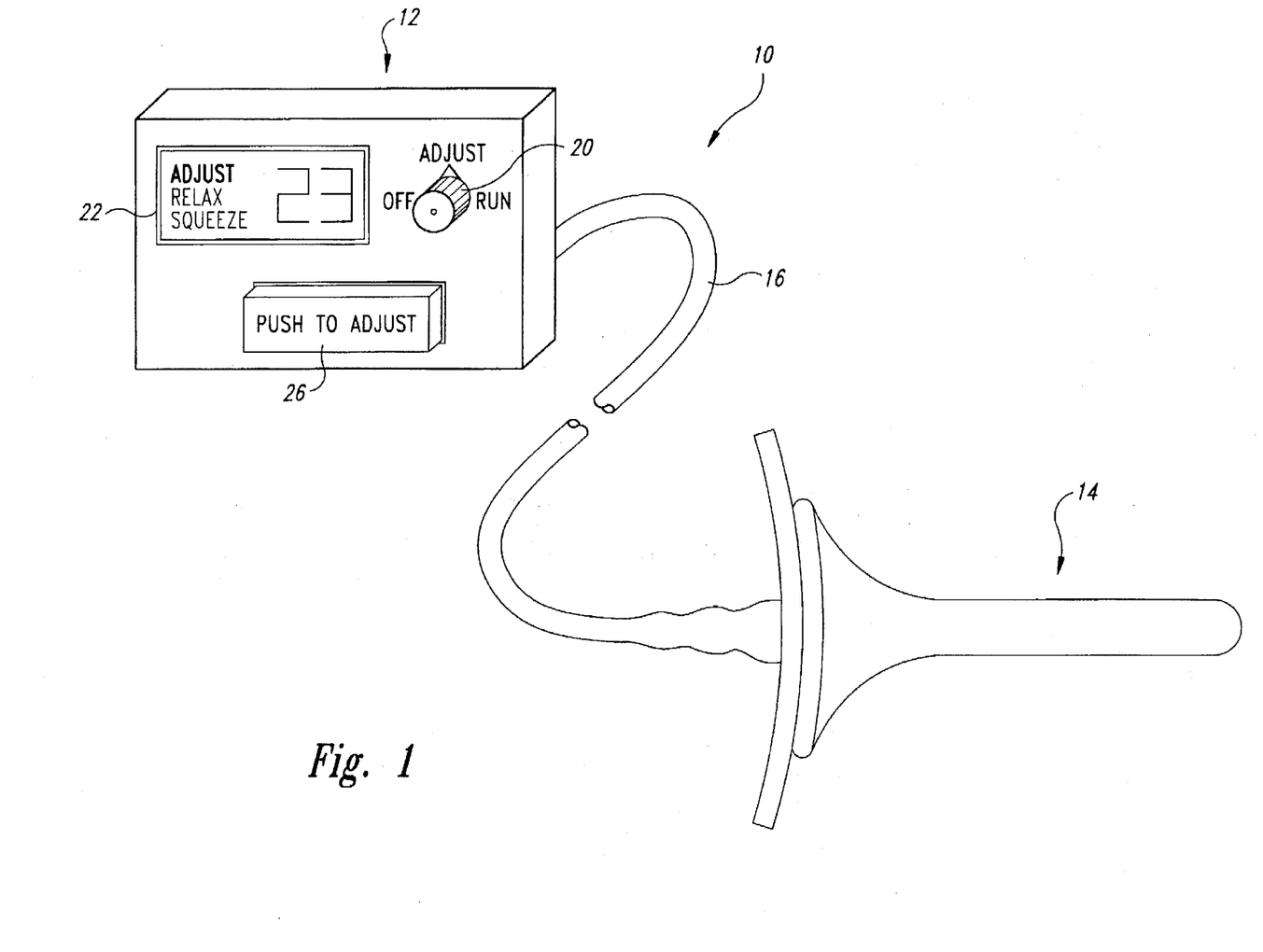
FIG. 1 is a perspective view of a perineometer in accordance with the present invention including a control module and a vaginal probe.

Referring now to the drawings in detail, wherein like numerals indicate the same elements throughout the views, FIG. 1 illustrates the perineometer of the present invention, generally shown at 10. Perineometer 10 includes control module 12 and vaginal probe 14. Vaginal probe 14 is pneumatically connected to control module 12 by flexible tube 16 of the appropriate length.

Control module 12 includes electric-pneumatic control switch 18 (described in connection with FIG. 5) which is operated by rotating control knob 20 between an OFF mode and two operational modes which include an ADJUST mode and a RUN mode. Visual display 22 includes indicia for indicating to a user when the control module is in the ADJUST mode or in the RUN mode. Display 22 also includes indicia conveying information to a user relating to the internal pressure of vaginal probe 14. Visual display 22 may be accompanied by or replaced by an audio display. For example, an audio display may be provided wherein the pitch of a tone is related to the vaginal pressure being exerted by the patient to provide visual and/or auditory feedback. An audio display accompanying or replacing visual display 22 or other audio displays may be provided which displays indicia by means of prerecorded or synthesized voice messages.

Control module 12 also includes air pump 24 (described in connection with FIG. 5) which is controlled by push bar 26. Air pump 24 is pneumatically connected to vaginal probe 14 through flexible tube 16. As will be described hereinafter, by operating push bar 26, vaginal probe 14 may be inflated and the pressure within the interior thereof controlled. Although air pump 24 is anticipated to be a manual pump which provides good controllability, automatic pumps may be used without departing from the teachings of this invention.

In use, vaginal probe 14 is inserted while in the uninflated preformed configuration into the patient's vagina, preferably by the patient herself. Control module 12 is placed in the ADJUST operational mode by rotating knob 20 appropriately. In this mode, visual display 22 will indicate that control module 12 is in the ADJUST mode, thereby instructing a user to inflate vaginal probe 14 by operating push bar 26. While vaginal probe 14 is being inflated, visual display 22 may indicate the pressure within probe 14 by displaying indicia which are proportional to that pressure. Such indicia may indicate the pressure numerically in pounds per square inch, or by means of other numbers which are proportional to pounds per square inch, or by means of a bar graph, or by means of other similar indicia. When the pressure within vaginal probe 14 reaches a predetermined base pressure, visual display 22 will so indicate, thereby instructing a user to cease operation of push bar 26. This communication may be effected for example by displaying the word "adjust" constantly when the pressure within probe 14 is below the predetermined base level, and thereafter flashing the word "adjust" when the pressure has reached or is above the predetermined base level. A patient may also cease operation of pump 24 in response to the pressure exerted against the walls of her vagina. If pump 24 is an automatic pump, it will automatically cease operation when the pressure in vaginal probe 14 reaches the predetermined base pressure.

An appropriate base level pressure is any pressure at which the probe 14 will not slip out of a patient's vagina during contraction of her vaginal musculature and which does not cause excessive discomfort. It is observed that these criteria encompass a wide range of base pressures. Because any base pressure within a wide range may be used and because the criteria for selecting an appropriate base pressure are neither precise nor sophisticated, a patient can easily select a working base pressure at home without assistance.

It is nevertheless anticipated that a patient may optimize her selection of a base level pressure by commissioning a health care professional to assist her in finding the pressure at which probe 14 is most comfortable. Further, with the assistance of persons experienced with the operation of the device, factors in addition to comfort can be considered in pinpointing an optimum base level pressure. For example, it is anticipated that persons experienced with the device (who may include, after time, patients themselves) will be able to select with accuracy base level pressures at which pressure changes in the probe 14 are optimally responsive to and optimally representative of actual contractions of a patient's vaginal musculature.

Once a base level pressure has been determined for a patient, the patient should refrain from varying that determined pressure over the course of her use of the device. By using the same base pressure day in and day out, measurements made on different days can be compared to one another and changes in a patient's performance over time can be observed.

After probe 14 has been pumped to an appropriate base level pressure in accordance with the preceding criteria, control module 12 is placed in the RUN operational mode by rotating knob 20. Visual display 22 thereafter indicates to a patient when to contract her vaginal muscles and when to relax her vaginal muscles according to predetermined time periods or other criteria such as the strength of her vaginal contractions. Thus are defined alternating periods of exercise and periods of rest to which the patient responds in order to optimize her performance of muscle contractions. While in the RUN operational mode, visual display 22 also displays indicia which are indicative of the interior pressure of vaginal probe 14. During an exercise period indicia are displayed which are proportional to the difference between the pressure within probe 14 during that exercise period and the average pressure within probe 14 during the preceding rest period. Because rapid fluctuations in pressure within vaginal probe 14 may occur during an exercise period, it is preferred that visual display 22 display a smooth or short-term averaged pressure difference rather than an instantaneous pressure difference so as to allow a user to read the display more easily. In instances where the instantaneous pressure difference is desirable, means may be provided to change the ballistics of the display to yield instantaneous values.

During periods of rest which follow the periods of exercise, display 22 displays indicia which are proportional to the difference between the average pressure within vaginal probe 14 during the immediately preceding exercise period and the average pressure within probe 14 during the immediately preceding rest period.

The exercise regimen most effective in strengthening the vaginal muscles will vary from patient to patient. For example, different patients may require periods of exercise of different duration, or a different number of exercise periods in a day's regimen. Furthermore, the attributes of a patient's optimally effective exercise regimen are expected to change over time, and in some cases, a patient may be best served by varying her exercise regimen from day to day or otherwise.

Accordingly, control module 12 includes control means for adjusting the characteristics of the rest and exercise periods encountered during the device's RUN operational mode. A user may adjust the duration of the rest or exercise periods directly, or instead, may activate further control means causing the duration of the rest and/or exercise periods to vary in response to the patient's performance. For example, a user may activate a control means causing an exercise period to terminate when a patient achieves a certain target pressure during contraction of her vaginal muscles; or that terminates in the alternative when a patient sustains a target pressure for a prescribed period of time.

Control module 12 also indicates to a user when the complete exercise regimen is finished. This may be accomplished according to a preset time or a predetermined number of exercise cycles which may be varied through appropriate control means, or may also be determined by control module 12 in response to other criteria such as the actual performance of the patient during the exercise regimen.

When exercising is terminated, control module 12 is placed in the OFF mode by rotating knob 20. This allows the pressure within vaginal probe 14 to be released, thereby deflating probe 14. Once probe 14 has been deflated, it may be easily removed by a patient from her vagina.

Figure 2A:
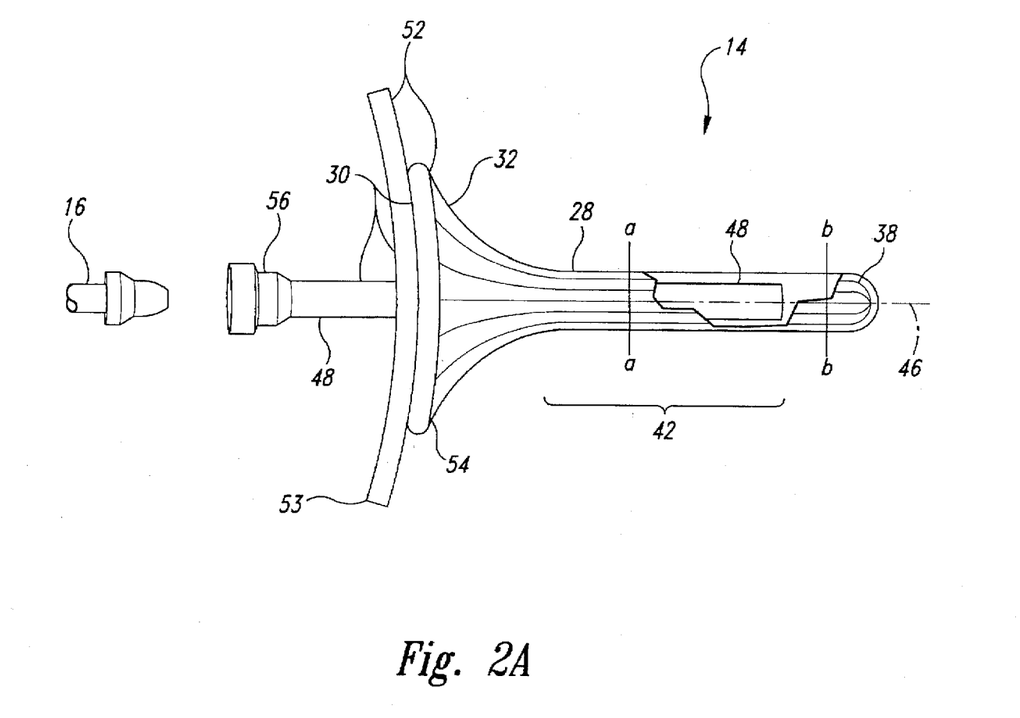
FIG. 2a is a side elevational view of a vaginal probe according to the present invention, approximately to scale, shown in its preformed uninflated configuration.
Figure 2B:
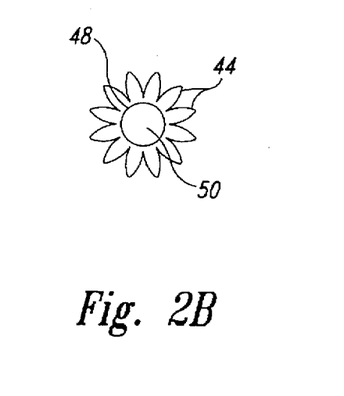
Figure 3A:
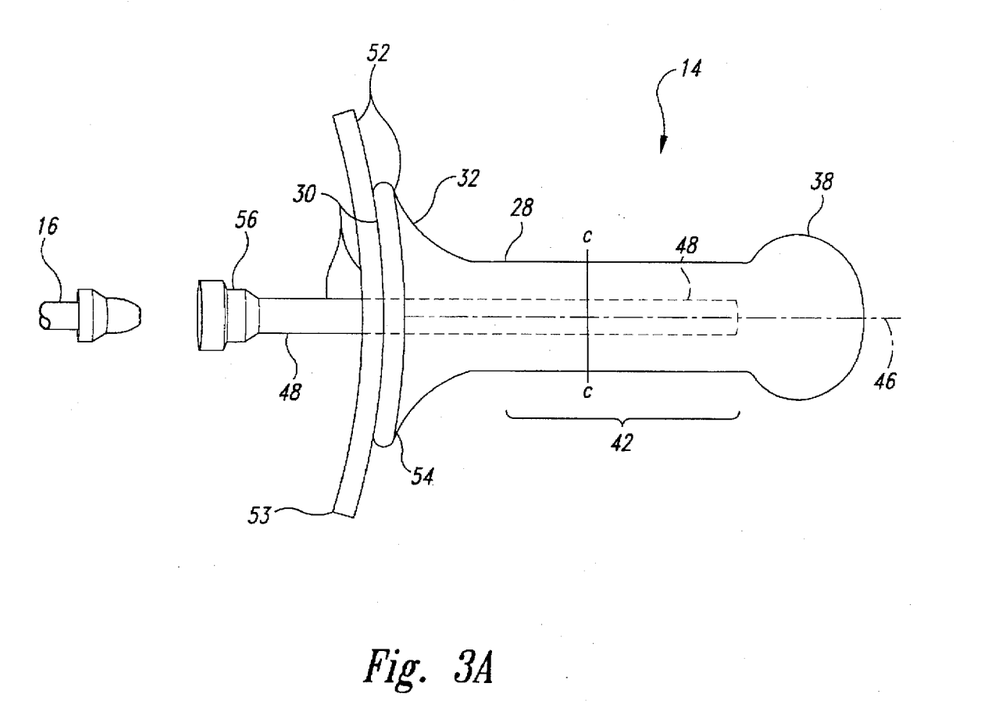
FIG. 3a is a side elevational view of a vaginal probe, approximately to scale, in an unconstrained expanded configuration.
Figure 3B:
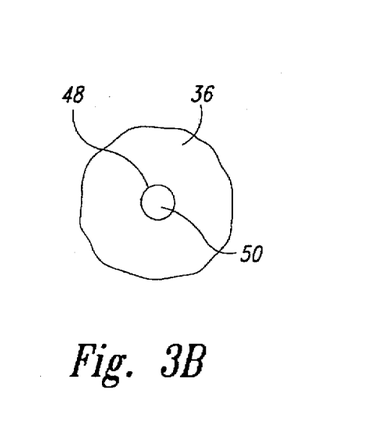
Figure 4A:
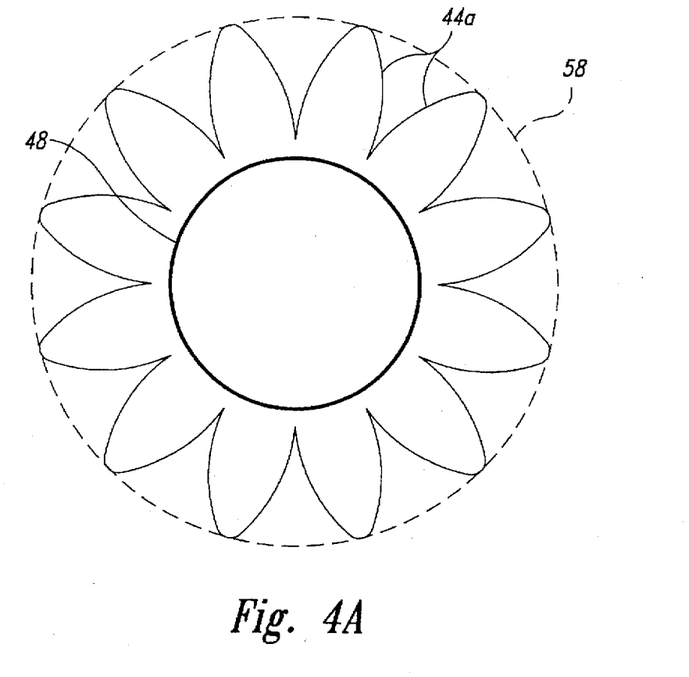
Figure 4B:
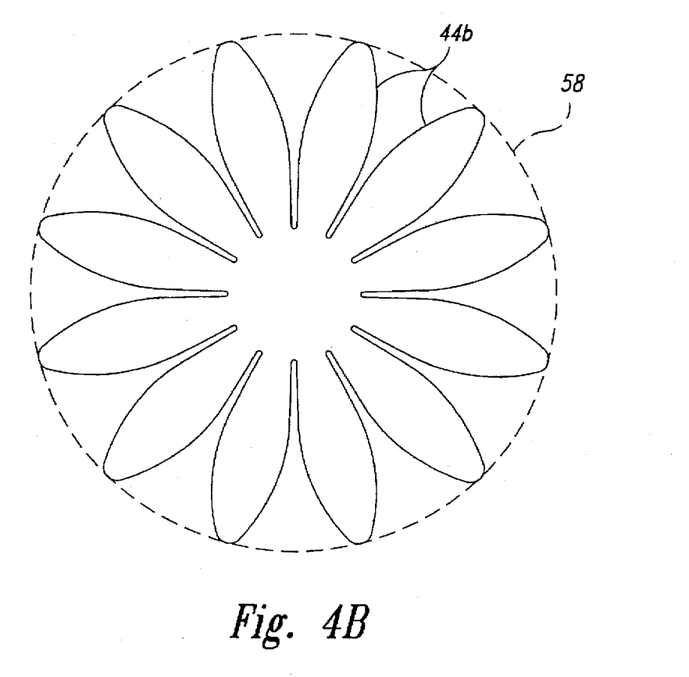

Referring now to FIGS. 2 and 3, vaginal probe 14 comprises an inflatable flaccid and expandable balloon 28 and a relatively rigid supporting frame 30. Balloon 28 has first end 32 defining an opening which communicates with the interior 36 of balloon 28. Second end 38 is a closed end as shown which separates interior 36 from the ambient air outside and surrounding balloon 28. Interposed between second end 38 and first end 32 is intermediate portion 42. Balloon 28 includes a plurality of longitudinal rib-like bellows 44 which are formed continuously from first end 32 along the lengths of intermediate portion 42 and second end 38. As shown by FIGS. 4a and 4b, bellows 44 are disposed radially along these lengths with respect to axis 46 of balloon 28.

Returning to FIGS. 2 and 3, relatively rigid frame 30 includes tube 48 which has a hollow interior 50. Flange 52 is disposed intermediate the ends of tube 48, and has a generally curved cross-section. Flange 52 includes plate 54 which provides a means for securing first end 32 of balloon 28 thereto. Preferably, first end 32 is stretched about the circumference of plate 54 and plate 54 is secured to the main flange body 53. Plate 54 and the main flange body 53 work together as a clamp to secure the balloon 28 to the flange 52 in fluid tight connection. A portion of tube 48 is disposed in interior 36, and supports bellows 44a disposed along the length of intermediate portion 42 (see also FIG. 4a). Tube 48 does not extend under bellows 44b disposed along the length of second end 38. As shown in FIGS. 2b and 4a, when balloon 28 is in the preformed natural uninflated configuration, tube 48 supports bellows 44a along the length of their interior surface at their smallest diameter.

On the opposite side of flange 52 from balloon 28, tube 48 has an end 56 which is contoured for detachably receiving and securing flexible tube 16 thereto. This attachment may also be accomplished by other means as is well known in the art, such as circumferential rings or ribs, as well as clamps.

However, for simplicity and ease of disassembly for use with the disposable vaginal probe 14, tube 48 should hold flexible tube 16 securely enough to withstand the anticipated pressures within interior 36 of balloon 28, but loosely enough to enable flexible tube 16 to be detached by hand.

Figure 5:
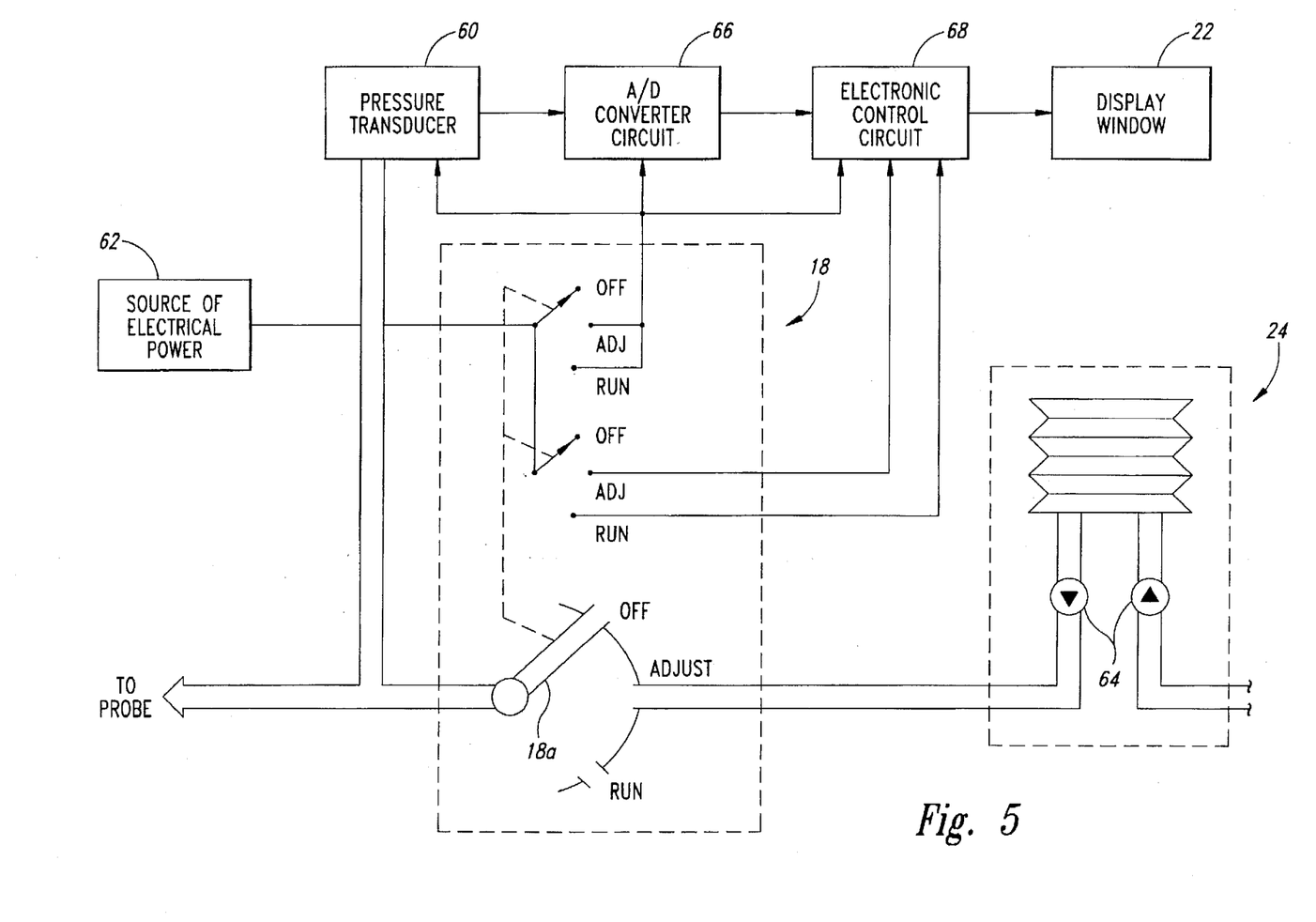
FIG. 5 is a block diagram of the control module of the present invention.

Referring now to FIGS. 3 and 5, when air is pumped into interior 36 of balloon 28, through interior 50 of tube 48, balloon 28 expands to an unconstrained expanded configuration, with second end 38 having a larger unconstrained effective perimeter than the unconstrained effective perimeter of intermediate portion 42. The air is pumped through flexible tube 16 to the interior 50 of tube 48, through the open end of tube 48 shown in FIG. 2a, to the interior 36 of ballon 28. The bulbous shape of second end 38, when in a vagina, acts upon the walls of the vagina to hold vaginal probe 14 securely therein such that it will not slip out during muscle contraction. As would be obvious to one of ordinary skill in the art, the unconstrained expanded configuration and unconstrained effective perimeters as illustrated in FIGS. 3a and 3b do not represent the shape that balloon 28 would assume when placed in a vagina and then inflated. In use, balloon 28 will substantially conform to the shape of the vagina. However, the shape of the vagina allows second end 38 to exert forces on the walls of the vagina which tend to hold vaginal probe 14 therein. It noted that a single-sized probe can be custom fitted into a wide range of different-sized vaginas simply by varying the extent of inflation of the probe 14 as discussed in connection with FIG. 1.

Returning to FIG. 3, which depicts the probe 14 in the unconstrained expanded configuration, second end 38 and intermediate portion 42 have substantially circular cross-sections which are aligned with each other. The large diameter of expanded second end 38 is approximately 1 and ½ times the diameter of expanded intermediate portion 42. This difference in diameter, which is related to the difference between the unconstrained effective perimeters of intermediate portion 42 and second end 38, may be accomplished in several ways. In the preformed uninflated configuration of the preferred embodiment, longitudinal bellows 44a disposed along the length of second end 38 are continuous with longitudinal bellows 44b disposed along the length of intermediate portion 42, with all bellows having a substantially uniform and constant effective outside diameter defined generally by dashed circle 58 in FIGS. 4a and 4b. However, along the length of end portion 38, bellows 44b are deeper than bellows 44a, as illustrated by a comparison between FIGS. 4b and 4a. The deeper bellows 44b provide more actual perimeter at second end 38 which results in second end 38 having a larger effective diameter than intermediate portion 42 in the unconstrained expanded configuration. While balloon 28 is anticipated to be formed of an elastomeric material, it may be simply formed of a flexible material since bellows 44 allow for the expansion of balloon 28 between the preformed uninflated configuration shown in FIGS. 2a and 2b to the expanded configuration shown in FIGS. 3a and 3b. Also, alternatively, bellows 44 may be omitted and balloon 28 formed of an elastomeric material having a greater expansion rate at second end 38 than along intermediate portion 42.

As stated above, second end 38 has a greater unconstrained effective perimeter than intermediate portion 42 when in the unconstrained expanded configuration. Since the preferred embodiment of the present invention includes longitudinal bellows 44, in the unconstrained expanded configuration balloon 28 may not assume an exactly or substantially circular cross-section. In other words, bellows 44 may still be identifiable in the expanded configuration depending upon the wall thickness of balloon 28, the interior pressure of probe 14 and the specific formation of the longitudinal bellows. If balloon 28 is made of a nonelastic material, its actual perimeter will not change between the natural preformed uninflated configuration and the unconstrained expanded configuration due to the bellows; however, as is easily observable, the effective perimeter of the balloon will still increase as the balloon 28 is inflated. In the preformed uninflated configuration, the effective perimeters of second end 38 and intermediate portion 42 are equal to each other and described by dashed line 58 in FIGS. 4a and 4b. If balloon 28 is fully inflated such that it has a substantially circular cross-section, then the effective perimeter at each point along the length of the balloon will be equal to the actual perimeter. However, if bellows 44 are still discernible in the expanded configuration, the effective perimeter will be defined by a circle similar to circle 58 located about the high points of bellows 44.

A simple set of formulas relates the dimensions of longitudinal bellows 44 of balloon 28 in the preformed uninflated configuration to the dimensions of tube 48 and of balloon 28 in the unconstrained fully-expanded configuration. In the description which follows:

$d_1$=outer diameter of tube 48

$d_2$=diameter of dashed circle 58 around balloon 28 in its preformed uninflated configuration $d_3$=diameter of the effective perimeter of intermediate portion 42 in the unconstrained expanded configuration $d_4$=diameter of the effective perimeter of second end 38 in the unconstrained expanded configuration $h_1$=uniform depth of longitudinal bellows 44b $h_2$=uniform depth of longitudinal bellows 44a N=number of complete (i.e., 2-sided) bellows then the following formulas apply:

$$h_2 \approx (d_2 - d_1)/2$$

$$d_3 \approx (2Nh_2)/\pi = N(d_2 - d_1)/\pi$$

$$d_4 \approx (2Nh_1)/\pi$$

In the exemplary embodiment shown in FIGS. 2–4, $d_1 \approx ½$ cm $d_2 \approx 1$ cm $d_3 \approx 2$ cm $d_4 \approx 3$ cm $h_1 \approx ⅜$ cm $h_2 \approx ¼$ cm

N=12

Referring to FIG. 5, control module 12 includes pressure transducer 60 which, in use, is in fluid communication with vaginal probe 14 so as to measure the pressure therein and generate an analog signal which is proportional to that pressure. Pressure transducer 60 could comprise an inexpensive piezoelectric or piezo-resistive crystal, mounted within an appropriate pneumatic housing inside control module 12.

Control module 12 is connected to a source of electrical power 62, such as an electrical outlet, or batteries. Switch 18 is disposed to place control module 12 in either the OFF mode or in one of two operational modes, an ADJUST mode and a RUN mode. As described above, in use, switch 18 is rotated to the ADJUST mode after vaginal probe 14 is inserted into the vagina. In the ADJUST mode, pneumatic switch 18a places probe 14 in fluid communication with air pump 24. Pump 24 includes two one-way check valves 64 which allow air to be pumped into interior 36 of probe 14 from the ambient. When the pressure signal from pressure transducer 60, which is converted to a digital signal by analog-to-digital converter 66, exceeds a predetermined level, electronic control circuit 68, which may be an integrated circuit microprocessor, causes visual display 22 to so indicate. Switch 18 is then turned by a user to the RUN mode, wherein electronic control circuit 68 causes visual display 22 to indicate alternating periods of exercise and periods of rest of a predetermined length of time. In this mode, electronic control circuit 68 causes visual display 22 to function as described above in response to the pressure signal from pressure transducer 60. When the total predetermined time for exercising has elapsed, or when other predetermined criteria have been met, display 22 indicates that the exercise regimen is completed. A user then rotates switch 18 to the OFF position which allows probe 14 to deflate by placing interior 36 in fluid communication with the ambient through pneumatic switch 18a. Probe 14 can then be easily removed from the patient's vagina by the patient herself.

After use, vaginal probe 14 may be cleaned and sanitized for the next exercise cycle, but preferably has been constructed inexpensively enough that the entire probe 14 may be simply discarded. Alternatively, balloon 28 of probe 14 may be discarded, while frame 30 is retained so that fresh replacement balloons 28 may be attached thereto.

In summary, numerous benefits have been described which result from employing the concepts of the invention. The improved perineometer described herein provides reliable biofeedback information to which a patient can respond to improve the efficiency of her exercises. A vaginal probe has been described which may be inflated so that it retains its position in the vagina without being ejected in response to contraction of the muscles. The pressure within the probe varies in response to the contraction of the muscles of the vagina. The control module indicates alternating periods of exercise and rest, along with indicia which vary concomitantly with the pressure inside of the probe. This perineometer may be used by an ordinary person without special training and provides an inexpensive device for home use.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application, to thereby enable one of ordinary skill in the art to best utilize the invention in various embodiments and with various modifications as are suited to the particular use contemplated. It is intended that the scope of the invention be defined by the claims appended hereto.

We claim:

1. A perineometer, comprising:
   (a) an inflatable vaginal probe with an interior pressure which may be varied by the contraction of a patient's vaginal muscles;
   (b) a pressure transducer for sensing the interior pressure of said probe;
   (c) a control module comprising:
      (i) an electronic control circuit and a display means;
      (ii) whereby said display means indicate alternating periods of exercise and periods of rest according to predetermined criteria;
      (iii) whereby said display means indicate during each of said periods of exercise indicia which are representative of the difference between the pressure within said probe during said exercise period and a first predetermined pressure;
      (iv) whereby said display means indicate during each of said rest periods indicia which are a function of the pressure within said probe during a plurality of preceding exercise periods and a second predetermined pressure;
   (d) wherein said probe is in fluid communication with said pressure transducer and said pressure transducer produces a signal which is transmitted to said control module.

2. The perineometer of claim 1, wherein said first predetermined pressure is determined from the average pressure within said probe during a preceding rest period.

3. The perineometer of claim 1, wherein said second predetermined pressure is determined from the average pressure within said probe during a preceding rest period.

4. The perineometer of claim 1, wherein said vaginal probe comprises:
   (a) a frame;
   (b) an inflatable balloon supported by said frame comprising:
      (i) a first open end attached to said frame with a fluid-tight connection;
      (ii) a second closed end;
      (iii) an intermediate portion disposed intermediate said first open end and said second closed end;
      (iv) wherein said balloon is inflatable from a preformed configuration to an expanded configuration;
      (v) wherein, while said balloon is in said expanded configuration, said second closed end has a perimeter which is larger than the perimeter of said intermediate portion.

5. The perineometer of claim 4, wherein said balloon includes a plurality of longitudinal bellows.

6. The perineometer of claim 5, wherein said longitudinal bellows are disposed radially.

7. The perineometer of claim 6, wherein, while said balloon is in said preformed configuration, said intermediate portion and said second closed end have a substantially uniform outside diameter which is substantially constant along the length of said intermediate portion and said second closed end.

8. The perineometer of claim 7, wherein said bellows are disposed along a portion of the length of said intermediate portion and said bellows are disposed along a portion of said second closed end.

9. The perineometer of claim 8, wherein the depth of said bellows disposed on said second closed end is greater than the depth of said bellows disposed on said intermediate portion.

10. The perineometer of claim 8 wherein said bellows are disposed continuously along the length of said intermediate portion and said second closed end.

11. The perineometer of claim 1, wherein said probe comprises an inflatable balloon having an interior, and wherein said control module further comprises means for inflating said balloon, said means being in fluid communication with said interior of said balloon.

12. The perineometer of claim 11, wherein said control module is operable in an adjust mode and a run mode; whereby said display means indicates, while said control module is in said adjust mode, when the pressure within said probe is greater than a third predetermined pressure.

13. A perineometer comprising:
   (a) an inflatable balloon comprising:

(i) a first open end;
(ii) a second closed end;
(iii) an intermediate portion interposed between said first open end and said second closed end;
(iv) an interior portion;
(v) wherein said balloon is inflatable from a preformed configuration to an expanded configuration wherein, while said balloon is in said expanded configuration, said second closed end has a perimeter which is larger than the perimeter of said intermediate portion;

(b) a frame, wherein said first open end of said balloon is attached to said frame with a fluid-tight connection; and (c) a control module including a pressure transducer and a display, said pressure transducer having an input and generating an output, said input of said pressure transducer being in fluid communication with said interior portion of said balloon, said control module further including a control switch for adjusting a fluid pressure in said interior portion of said balloon, said display presenting indicia derived at least in part from said output of said pressure transducer.

14. The perineometer of claim 13 wherein said frame comprises a flange, whereby said first open end of said balloon is attached to said flange.

15. The perineometer of claim 13 wherein said frame further comprises a hollow tube having an interior which is in fluid communication with said interior portion of said balloon.

16. The perineometer of claim 13 wherein said balloon further comprises a plurality of longitudinal bellows formed in a portion of said balloon.

17. The perineometer of claim 16 wherein said longitudinal bellows are disposed radially.

18. The perineometer of claim 16 wherein said frame comprises:

(a) a hollow tube having an interior which is in fluid communication with said interior portion of said balloon, wherein said tube is partially disposed within said interior portion of said balloon; and (b) a flange disposed on said tube wherein said first open end of said balloon is attached to said flange.

19. The perineometer of claim 18 wherein, when said balloon is in said preformed configuration, said tube supports said bellows.

20. The perineometer of claim 18 wherein said bellows are disposed along a length of said intermediate portion and along a portion of said second closed end, and wherein the depth of said bellows disposed along said second closed end is greater than the depth of said bellows disposed along said intermediate portion.

21. The perineometer of claim 20 wherein said bellows are disposed continuously along said intermediate portion and said bellows are disposed along a portion of said second closed end, and wherein said intermediate portion and said second closed end have a substantially uniform outside diameter while said balloon is in said preformed configuration.

22. A perineometer comprising:
an inflatable balloon mounted on a frame said balloon comprising:
(a) a first open end;
(b) a second closed end;
(c) an intermediate portion interposed between said first open end and said second closed end;
(d) an interior portion;

(e) wherein said balloon is inflatable from a non-expanded configuration to an expanded configuration;
(f) wherein, while said balloon is in said expanded configuration, said second closed end has a perimeter greater than the perimeter of said intermediate portion; and a control module including pressure transducer and a display, said pressure transducer having an input generating an output, said input of said pressure transducer being in fluid communication with said interior portion of said balloon, said control module further including a control switch for adjusting pressure in said interior portion of said balloon, said display indicia derived at least in part from said output of said pressure transducer.

23. The perineometer of claim 22, further comprising a plurality of longitudinal bellows formed along the length of a portion of said balloon.

24. The perineometer of claim 23, wherein said longitudinal bellows are radially disposed along a portion of the length of said intermediate portion and along a portion of the length of said second closed end.

25. The perineometer of claim 24, wherein said intermediate portion and said second closed end have a substantially uniform outside diameter while said balloon is in said non-expanded configuration.

26. The perineometer of claim 25, wherein the depth of said bellows disposed along the length of said second closed end is greater than the depth of said bellows disposed along the length of said intermediate portion.

27. The perineometer of claim 26, wherein said bellows are formed continuously along the length of said intermediate portion and the length of said second closed end.

28. The perineometer of claim 22, wherein, while said balloon is in said expanded configuration, the diameter of said second closed end is approximately one and one-half times the diameter of said intermediate portion.

29. The perineometer of claim 22 wherein said frame comprises:

(a) a tube comprising a hollow interior, a first open end, and a second open end, wherein both of said ends are in fluid communication with said interior portion of said balloon;

(b) a flange interposed between said ends, said flange including means for connecting said balloon thereto in a fluid-tight connection.

30. A control module for use with a perineometer, said perineometer comprising an inflatable vaginal probe whose interior pressure may be varied by the contraction of a patient's vaginal muscles, wherein said control module comprises:

(a) a pressure transducer for sensing the pressure in said probe;

(b) an electronic control circuit;

(c) display means;

(d) wherein said display means indicates periods of exercise and periods of rest, wherein said periods of exercise alternate with said periods of rest according to predetermined criteria;

(e) wherein said display means indicate indicia which are representative of the difference between the pressure in said probe during a present period of exercise and the average pressure in said probe during a preceding period of rest;

(f) wherein said display means indicate indicia which are representative of the difference between the average pressure in said probe during a preceding period of exercise and the average pressure in said probe during a preceding period of rest.

31. The control module of claim 30, further comprising a pump for inflating said probe.

32. The control module of claim 31, wherein said control module is selectively operational in an adjust mode and a run mode, and wherein said display means indicates, while said control module is in said adjust mode, when the pressure within said probe is greater than a predetermined pressure.

33. A perineometer comprising:
a frame;
a flange;
a balloon;
wherein said balloon is comprised of:
a first open end;
a second closed end;
an intermediate portion;
an interior portion;
wherein said first open end is attached to said frame with a fluid-tight connection;
wherein said balloon is further comprised of a bellows having a plurality of folds;
wherein said folds extend along the length of said balloon from said first open end to said second closed end;
wherein the expanded perimeter of said second closed end is larger than the expanded perimeter of said intermediate portion; and
a control module including a pressure transducer and a display, said pressure transducer having an input and generating an output, said input of said pressure transducer being in fluid communication with said interior portion of said balloon, said control module further including a control switch for adjusting a fluid pressure in said interior portion of said balloon, said display presenting indicia derived at least in part from said output of said pressure transducer.

34. The perineometer of claim 33 wherein said balloon is comprised of an elastic material.

35. The perineometer of claim 33 wherein said balloon is comprised of an elastomeric material.

36. The perineometer of claim 33 wherein said balloon is comprised of a nonelastic material.

37. A perineometer comprising:
a probe, wherein said probe comprises:
a frame;
a flange;
a balloon;
wherein said balloon is comprised of:
a first open end;
a second closed end;
an intermediate portion;
an interior portion;
wherein said first open end is attached to said frame with a fluid-tight connection;
wherein the expanded perimeter of said second closed end is larger than the expanded perimeter of said intermediate portion;
wherein said balloon is comprised of an elastomeric material;
wherein the expansion rate of said second closed end is greater than the expansion rate of said intermediate portion; and
a control module including a pressure transducer and a display, said pressure transducer having an input and generating an output, said input of said pressure transducer being in fluid communication with said interior portion of said balloon, said control module further including a control switch for adjusting a fluid pressure in said interior portion of said balloon, said display presenting indicia derived at least in part from said output of said pressure transducer.

38. A perineometer comprising:
a probe, wherein said probe comprises:
a frame;
a flange;
a balloon;
wherein said balloon is comprised of:
a first open end;
a second closed end;
an intermediate portion;
an interior portion;
wherein said first open end is attached to said frame with a fluid-tight connection;
wherein the expanded perimeter of said second closed end is larger than the expanded perimeter of said intermediate portion;
wherein said balloon is comprised of an elastic material; and
a control module including a pressure transducer and a display, said pressure transducer having an input and generating an output, said input of said pressure transducer being in fluid communication with said interior portion of said balloon, said control module further including a control switch for adjusting a fluid pressure in said interior portion of said balloon, said display presenting indicia derived at least in part from said output of said pressure transducer.

39. The perineometer of claim 38 wherein said elastic material is an elastomeric material.

40. A perineometer, comprising:
(a) an inflatable vaginal probe with an interior pressure which may be varied by the contraction of a patient's vaginal muscles;
(b) a pressure transducer for sensing the interior pressure of said probe;
(c) a control module comprising:
(i) an electronic control circuit and a display;
(ii) said display indicating alternating periods of exercise and periods of rest according to a predetermined criteria;
(iii) said display indicating during each of said periods of exercise indicia which are representative of the difference between the pressure within said probe during said exercise period and a first predetermined pressure;
(iv) said display indicating during each of said rest periods indicia which are a function of the pressure within said probe during at least one preceding exercise period and a second predetermined pressure;
(d) wherein said probe is in fluid communication with said pressure transducer and said pressure transducer produces a signal which is transmitted to said control module.

41. A vaginal probe for use with a perineometer, said vaginal probe comprising:
(a) an inflatable balloon comprising:
(i) a first open end;
(ii) a second closed end;
(iii) an intermediate portion interposed between said first open end and said second closed end;

(iv) a plurality of longitudinal bellows formed in a portion of said balloon;

(v) wherein said balloon is inflatable from a preformed configuration to an expanded configuration such that while said balloon is in said expanded configuration, said second closed end has a perimeter which is larger than the perimeter of said intermediate portion;

(b) a frame, wherein said first open end of said balloon is attached to said frame with a fluid-tight connection.

42. The vaginal probe of claim 41 wherein said longitudinal bellows are disposed radially.

43. The vaginal probe of claim 41 wherein said frame comprises:

(a) a hollow tube having an interior which is in fluid communication with said balloon, wherein said tube is partially disposed within said balloon; and (b) a flange disposed on said tube wherein said first open end of said balloon is attached to said flange.

44. The vaginal probe of claim 43 wherein when said balloon is in said preformed configuration, said tube supports said bellows.

45. The vaginal probe of claim 43 wherein said bellows are disposed along a length of said intermediate portion and along a portion of said second closed end, and wherein the depth of said bellows disposed along said second closed end is greater than the depth of said bellows disposed along said intermediate portion.

46. The vaginal probe of claim 45 wherein said bellows are disposed continuously along said intermediate portion and said bellows are disposed along a portion of said second closed end, and wherein said intermediate portion and said second closed end have a substantially uniform outside diameter while said balloon is in said preformed configuration.

* * * * *